United States Patent
Cottrell et al.

(10) Patent No.: US 7,384,519 B2
(45) Date of Patent: Jun. 10, 2008

(54) PROCESS FOR THE PURIFICATION OF PHARMACEUTICAL GRADE HFC-134A AND POLYMER GRADE HCFC-22

(75) Inventors: Stephen A. Cottrell, Baton Rouge, LA (US); Robert E. Wilson, Denham Springs, LA (US)

(73) Assignee: Honeywell International Inc., Morristown, NJ (US)

( * ) Notice: Subject to any disclaimer, the term of this patent is extended or adjusted under 35 U.S.C. 154(b) by 651 days.

(21) Appl. No.: 10/745,085

(22) Filed: Dec. 23, 2003

(65) Prior Publication Data
US 2005/0133360 A1 Jun. 23, 2005

(51) Int. Cl.
*B01D 3/34* (2006.01)
*B01D 15/00* (2006.01)
*C02F 17/389* (2006.01)

(52) U.S. Cl. ............... 203/41; 203/29; 203/71; 210/690; 210/806; 570/178; 570/179

(58) Field of Classification Search ............... 203/29, 203/41, 71; 210/664, 690, 806; 570/177, 570/178, 179
See application file for complete search history.

(56) References Cited

U.S. PATENT DOCUMENTS

| | | | |
|---|---|---|---|
| 4,020,117 A | 4/1977 | Sisson et al. | |
| 5,035,794 A * | 7/1991 | Atwood | 208/262.1 |
| 5,069,887 A * | 12/1991 | Suenaga et al. | 95/128 |
| 5,261,948 A | 11/1993 | Foley et al. | 95/142 |
| 5,294,358 A * | 3/1994 | Dantinne et al. | 252/67 |
| 5,600,040 A | 2/1997 | Corbin et al. | 570/179 |
| 6,413,496 B1 | 7/2002 | Goodman et al. | |
| 6,458,249 B2 * | 10/2002 | Miller et al. | 203/51 |
| 2003/0155305 A1* | 8/2003 | Cook et al. | 210/692 |
| 2003/0191350 A1* | 10/2003 | Ohno et al. | 570/105 |

FOREIGN PATENT DOCUMENTS

DE 3311751 10/1984

OTHER PUBLICATIONS

XP002340979, Sep. 26, 2001, JP2001261330 (Tosoh Corp., Japan) Kawamoto, Taizo et al. "Zeolite bead moldings, and manufacture of sam for removal of impurities by absorption" from STN Database No. 2001:707120 abstract.
XP002246547, 1998, Ravindra K et al, "Absorption of Halocarbons on a Carbon Molecular Sieve", Microporous and Mesoporous materials, Elsevier Science Publishing, New York, US, vol. 22, 1998, pp. 281-288 ISSN: 1387-1811.

* cited by examiner

*Primary Examiner*—Virginia Manoharan
(74) *Attorney, Agent, or Firm*—Erika S. Wilson

(57) ABSTRACT

A method for the purification of pharmaceutical grade 1,1,1,2-tetrafluoroethane (HFC-134*a*) and polymer grade chlorodifluoromethane (HCFC-22) by contacting a mixture containing 1,1,1,2-tetrafluoroethane or chlorodifluoromethane and methyl chloride with a zeolite such as a molecular sieve, and recovering from said contacted mixture substantially purified 1,1,1,2-tetrafluoroethane or chlorodifluoromethane.

41 Claims, No Drawings

PROCESS FOR THE PURIFICATION OF PHARMACEUTICAL GRADE HFC-134A AND POLYMER GRADE HCFC-22

BACKGROUND OF THE INVENTION

The present invention relates to a process for the purification of pharmaceutical grade 1,1,1,2-tetrafluoroethane (HFC-134a) and for the purification of chlorodifluoromethane (HCFC-22) by the removal of impurities including methyl chloride.

Delivery of drugs to the lung by way of inhalation is an important means of treating a variety of conditions, including such common local conditions as cystic fibrosis, pneumonia, bronchial asthma and chronic obstructive pulmonary disease and some systemic conditions including pain management, immune deficiency, hormonal therapy, erythropoiesis, diabetes, etc. Such drugs are commonly administered to the lung as an aerosol of respirable size particles (less than about 10 µm in diameter). In order to assure proper particle size in the aerosol, particles can be prepared in respirable size and then incorporated into a colloidal dispersion containing a propellant, as a pressurized metered dose inhaler (MDI). Solutions of formulations must be dispensed in a manner that produces particles or droplets of respirable size. For MDI applications, a prepared aerosol formulation is filled into an aerosol canister equipped with a metered dose valve. The formulation is dispensed via an actuator adapted to direct the dose from the valve to the patient. Metered dose aerosol canisters deliver the medicine to be inhaled into the mouth, nasal areas or respiratory airways. Examples of metered dose inhalers are set forth in U.S. Pat. Nos. 5,544,647; 5,622,163 and 6,581,590.

HFC-134a is an environmentally acceptable potential replacement for chlorofluorocarbon refrigerants, blowing agents, aerosol propellants and sterilants that are being viewed with concern in connection with the destruction of stratospheric ozone. HFC-134a has been known as a propellant for a metered dose inhaler for pharmaceutical compositions. Pharmaceutical compositions comprising a pharmaceutically active agent in 1,1,1,2-tetrafluoroethane (HFC-134a) as a propellant, for delivery in aerosol form, and to a device for delivering such a composition as an aerosol are known from U.S. Pat. No. 6,413,496. The use of HFC-134a in such pharmaceutical applications requires that it be of extremely high purity, i.e. significantly more pure than that which would be more typically used in refrigeration. In meeting the specifications for pharmaceutical use, a key impurity to be removed is methyl chloride. The manufacture of pharmaceutical grade HFC-134a has been a problem since the desired pharmaceutical use makes purification by traditional distillation techniques difficult due to the presence of close boiling point methyl chloride impurities. This is because HFC-134a and methyl chloride differ in normal boiling point by only 3° C. This small difference in boiling point requires high reflux ratios in order to achieve separation. This process is extremely energy intensive and reduces the throughput capability of the manufacturing system. An improvement over the known methods to ensure a cost effective process would be desired.

HCFC-22 is a refrigerant which is useful for the production of tetrafluoroethylene monomer which is a precursor for the production of polytetrafluoroethylene (Teflon).

The inventive improvement provides a technique for removing methyl chloride from HFC-134a or HCFC-22 by contacting a mixture of methyl chloride and HFC-134a or HCFC-22 with a molecular sieve. This technique may also be used to remove methyl chloride and other impurities from a variety of halocarbons where separation by distillation or other means is impractical or inefficient. The use of molecular sieve for this separation substantially reduces energy requirements and does not show a reduction in throughput for the purification process. This results in a more cost effective alternative to conventional distillation techniques.

DESCRIPTION OF THE INVENTION

The invention provides a method for separating 1,1,1,2-tetrafluoroethane from a mixture comprising 1,1,1,2-tetrafluoroethane and methyl chloride which comprises contacting a mixture comprising 1,1,1,2-tetrafluoroethane and methyl chloride with a zeolite under conditions sufficient to remove the methyl chloride and then recovering from said contacted mixture substantially purified 1,1,1,2-tetrafluoroethane.

The invention also provides a method for preparing a pharmaceutical delivery form which comprises combining the substantially purified 1,1,1,2-tetrafluoroethane with a therapeutically effective amount of a pharmaceutical composition.

The invention further provides a method for separating chlorodifluoromethane from a mixture comprising chlorodifluoromethane and methyl chloride which comprises contacting a mixture comprising chlorodifluoromethane and methyl chloride with a zeolite under conditions sufficient to remove the methyl chloride and then recovering from said contacted mixture substantially purified chlorodifluoromethane.

In the production of 1,1,1,2-tetrafluoroethane and chlorodifluoromethane, certain by-products and impurities, especially methyl chloride, remain in mixture therewith and the vast majority of them are easily removable by standard techniques such as distillation, filtration, etc. However, typically small amounts of methyl chloride remain. Typically, these are on the order of about 20-25 parts per million by weight (ppmw). For pharmaceutical aerosol applications, this amount of methyl chloride must be reduced to amounts of about 5 ppmw or less, preferably about 1 ppmw or less and most preferably about 0 ppmw.

The methyl chloride may be reduced or removed from the 1,1,1,2-tetrafluoroethane or chlorodifluoromethane by contacting a mixture comprising 1,1,1,2-tetrafluoroethane or chlorodifluoromethane and methyl chloride with a zeolite under conditions sufficient to remove the methyl chloride and then recovering substantially purified 1,1,1,2-tetrafluoroethane or chlorodifluoromethane. The mixture is contacted with an excess of the zeolite under suitable conditions, which may be at atmospheric pressure, superatmospheric press or subatmospheric pressure, and at room or ambient temperatures, elevated temperatures or at reduced temperatures. The mixture contacts the zeolite for a few seconds, for example about 10 seconds or less and the methyl chloride becomes entrapped in the pores of the zeolite.

Zeolites are hydrated aluminosilicates of the alkaline and alkaline-earth metals which are microporous crystalline solids with well-defined structures. Generally they contain silicon, aluminum and oxygen in their framework and cations, water and/or other molecules within their pores. Zeolites are framework silicates having tetrahedrons of $SiO_4$ and $AlO_4$. In order to be a zeolite the ratio $(Si+Al)/O$ must equal ½. The alumino-silicate structure is negatively charged and attracts the positive cations that reside within. Zeolites have large vacant spaces or cages in their structures that allow space for large cations such as sodium, potassium, barium and calcium and even relatively large molecules and cation groups such as water, ammonia, carbonate ions and nitrate ions. In the more useful zeolites, the spaces are interconnected and form long wide channels of varying sizes depending on the mineral. These channels allow the easy movement of the resident ions and molecules into and out of the structure. Zeolites are characterized by their ability to lose and absorb water without damage to their crystal structures. Zeolites which are useful for this invention non-exclusively include:

Analcime (Hydrated Sodium Aluminum Silicate)
Pollucite (Hydrated Cesium Sodium Aluminum Silicate)
Wairakite (Hydrated Calcium Sodium Aluminum Silicate)
Bellbergite (Hydrated Potassium Barium Strontium Sodium Aluminum Silicate)
Bikitaite (Hydrated Lithium Aluminum Silicate)
Boggsite (Hydrated calcium Sodium Aluminum Silicate)
Brewsterite (Hydrated Strontium Barium Sodium Calcium Aluminum Silicate)
Chabazite (Hydrated Calcium Aluminum Silicate)
Willhendersonite (Hydrated Potassium Calcium Aluminum Silicate)
Cowlesite (Hydrated Calcium Aluminum Silicate)
Dachiardite (Hydrated calcium Sodium Potassium Aluminum Silicate)
Edingtonite (Hydrated Barium Calcium Aluminum Silicate)
Epistilbite (Hydrated Calcium Aluminum Silicate)
Erionite (Hydrated Sodium Potassium Calcium Aluminum Silicate)
Faujasite (Hydrated Sodium Calcium Magnesium Aluminum Silicate)
Ferrierite (Hydrated Sodium Potassium Magnesium Calcium Aluminum Silicate)
Amicite (Hydrated Potassium Sodium Aluminum Silicate)
Garronite (Hydrated Calcium Aluminum Silicate)
Gismondine (Hydrated Barium Calcium Aluminum Silicate)
Gobbinsite (Hydrated Sodium Potassium Calcium Aluminum Silicate)
Gmelinite (Hydrated Sodium Calcium Aluminum Silicate)
Gonnardite (Hydrated Sodium Calcium Aluminum Silicate)
Goosecreekite (Hydrated Calcium Aluminum Silicate)
Harmotome (Hydrated Barium Potassium Aluminum Silicate)
Phillipsite (Hydrated Potassium Sodium Calcium Aluminum Silicate)
Wellsite (Hydrated Barium Calcium Potassium Aluminum Silicate)
Clinoptilolite (Hydrated Sodium Potassium Calcium Aluminum Silicate)
Heulandite (Hydrated Sodium Calcium Aluminum Silicate)
Laumontite (Hydrated Calcium Aluminum Silicate)
Levyne (Hydrated Calcium Sodium Potassium Aluminum Silicate)
Mazzite (Hydrated Potassium Sodium Magnesium Calcium Aluminum Silicate)
Merlinoite (Hydrated Potassium Sodium Calcium Barium Aluminum Silicate)
Montesommaite (Hydrated Potassium Sodium Aluminum Silicate)
Mordenite (Hydrated Sodium Potassium Calcium Aluminum Silicate)
Mesolite (Hydrated Sodium Calcium Aluminum Silicate)
Natrolite (Hydrated Sodium Aluminum Silicate)
Scolecite (Hydrated Calcium Aluminum Silicate)
Offretite (Hydrated Calcium Potassium Magnesium Aluminum Silicate)
Paranatrolite (Hydrated Sodium Aluminum Silicate)
Paulingite (Hydrated Potassium Calcium Sodium Barium Aluminum Silicate)
Perlialite (Hydrated Potassium Sodium Calcium Strontium Aluminum Silicate)
Barrerite (Hydrated Sodium Potassium Calcium Aluminum Silicate)
Stilbite (Hydrated Sodium Calcium Aluminum Silicate)
Stellerite (Hydrated Calcium Aluminum Silicate)
Thomsonite (Hydrated Sodium Calcium Aluminum Silicate)
Tschernichite (Hydrated Calcium Aluminum Silicate)
Yugawaralite (Hydrated Calcium Aluminum Silicate)

Preferred zeolites are those which are characterized as molecular sieves. Molecular sieves are well known in the art and are defined in R. Szosak, Molecular Sieves-Principles of Synthesis and Identification, Van Nostrand Reinhold (1989) page 2, which is incorporated herein by reference. The Sanderson electronegativity model (see, R. T. Sanderson, "Chemical Bonds and Bond Energy", 2nd ed., Academic Press, New York, 1976), which is incorporated herein by reference, furnishes a useful method for classifying inorganic molecular sieves based on their chemical composition.

This invention can be practiced with the zeolite contained in a stationary packed bed through which the process stream whose components need separation is passed. Alternatively, it can be practiced with the zeolite applied as a countercurrent moving bed; or with a fluidized bed where the sorbent itself is moving. It can be applied with the zeolite contained as a stationary packed bed but the process configured as a simulated moving bed, where the point of introduction to the bed of the process stream requiring separation is changed, such as may be effected using appropriate switching valves. The most preferred of which is molecular sieve 4A which has the formula $Na_2O$—$Al_2O_3$-$2SiO_2$-$nH_2O$ (CAS# 70955-01-0).

For the purification of 1,1,1,2-tetrafluoroethane, the molecular sieve contacting process may be preceded and/or followed by one or more distillation steps to remove impurities having a higher boiling point than 1,1,1,2-tetrafluoroethane, a lower boiling point than 1,1,1,2-tetrafluoroethane or both. If desired, an additional subsequent step may be conducted by contacting the purified 1,1,1,2-tetrafluoroethane with molecular sieve again.

The prior and/or subsequent 1,1,1,2-tetrafluoroethane distillations may be conducted, in either order, by feeding the 1,1,1,2-tetrafluoroethane into a first distillation column. During this step low boiling impurities, i.e., monochloropentafluoroethane (CFC-115), monochlorotrifluoromethane (CFC-13), 1,1,1-trifluoroethane (HFC-143a), monochlorodifluoromethane (HCFC-22) and other lights are purged overhead as a vapor to the atmosphere. Bottoms from this step, i.e., 1,1,1,2-tetrafluoroethane without light impurities are fed out of the reboiler into an intermediate container or directly to a second column for high boiling impurity removal. If an intermediate container is used, then once it is full, it is circulated and sampled to determine whether the material meets the final product specification for lights. If the light impurities are not in specification this distillation can be repeated for light impurity removal. If the light impurities are within specification, then the resulting material is fed to a second distillation column for the second purification step. During this step high boiling impurities, i.e., trichlorotrifluoroethane (CFC-113), 1,2-dichloro-1,1,2,2-tetrafluoroethane (CFC-114) 1,1,2,2 tetrafluoroethane (HFC-134) and other high boiling impurities are purged as a liquid from the reboiler. High purity HFC-134a from overhead is gravity fed or pumped to a product container. If the analytical results are out of specification for methyl chloride, or for moisture then an additional contacting with molecular sieve may be done. The result is circulated through the molecular sieve, sampled and analyzed until it is within product specifications.

The distillation conditions for removal of light and heavy impurities are not critical. Typically, a distillation for the removal of light impurities may be conducted at a pressure of from about 0 psig to about 400 psig, preferably from about 60 psig to about 200 psig, and more preferably from about 90 psig to about 100 psig. For this distillation, the temperature may range from about −45° F. to about 210° F., preferably from about 40° F. to about 150° F., and more preferably from about 82° F. to about 88° F. For this distillation, the reflux ratio may range from about 20:1 to about 500:1, preferably from about 50:1 to about 200:1 and more preferably from about 80:1 to about 120:1. Reflux ratio is the ratio of condensed overhead liquid returned to the column to the vapor exiting the column expressed either as a mass or molar ratio. For this distillation the number of distillation stages may range from about 25 to about 200, preferably from about 30 to about 150 and more preferably from about 50 to about 60.

Typically, a distillation for the removal of heavy impurities may be conducted at a pressure of from about 0 psig to about 400 psig, preferably from about 100 psig to about 250 psig, and more preferably from about 190 psig to about 210 psig. For this distillation, the temperature may range from about −45° F. to about 210° F., preferably from about 70° F. to about 170° F., and more preferably from about 127° F. to about 134° F. For this distillation, the reflux ratio may range from about 2:1 to about 50:1, preferably from about 5:1 to about 30:1 and more preferably from about 8:1 to about 12:1. For this distillation the number of distillation stages may range from about 20 to about 200, preferably from about 30 to about 150 and more preferably from about 50 to about 60.

For the purification of chlorodifluoromethane, the molecular sieve contacting process may be preceded and/or followed by one or more distillation steps to remove impurities having a higher boiling point than chlorodifluoromethane, a lower boiling point than chlorodifluoromethane or both. If desired, an additional subsequent step may be conducted by contacting the purified chlorodifluoromethane with molecular sieve again.

The prior or subsequent chlorodifluoromethane distillations may be conducted, in either order, by feeding the chlorodifluoromethane into a first distillation column. During this step low boiling impurities, i.e., trifluoromethane, (HFC-23), are purged overhead as a vapor to the atmosphere. Bottoms from this step, i.e., chlorodifluoromethane without light impurities are fed out of the reboiler into an intermediate container or directly to a second column for high boiling impurity removal. If the intermediate container is used, then once it is full, it is circulated and sampled to determine whether the material meets the final product specification for lights. If the light impurities are not in specification this distillation can be repeated for light impurity removal. If the light impurities are within specification, then the resulting material is fed to a second distillation column for the second purification step. During this step high boiling impurities, i.e., dichlorofluoromethane (HCFC-21), methyl chloride are purged as a liquid from the reboiler. High purity HCFC-22 from overhead is gravity fed or pumped to a product container. If the analytical results are out of specification for methyl chloride, or for moisture then an additional contacting with molecular sieve may be done. The result is circulated through the molecular sieve, sampled and analyzed until it is within product specifications.

The distillation conditions for removal of light and heavy impurities from chlorodifluoromethane are not critical. Typically, a distillation for the removal of light impurities may be conducted at a pressure of from about 0 psig to about 400 psig, preferably from about 100 psig to about 250 psig, and more preferably from about 145 psig to about 150 psig. For this distillation, the temperature may range from about −95° F. to about 60° F., preferably from about −30° F. to about 20° F., and more preferably from about −15° F. to about −10° F. For this distillation, the reflux ratio may range from about 2:1 to about 500:1, preferably from about 5:1 to about 200:1 and more preferably from about 10:1 to about 20:1. For this distillation the number of distillation stages may range from about 20 to about 200, preferably from about 30 to about 100 and more preferably from about 30 to about 40.

Typically, a distillation for the removal of heavy impurities from chlorodifluoromethane may be conducted at a pressure of from about 0 psig to about 400 psig, preferably from about 100 psig to about 250 psig, and more preferably from about 135 psig to about 145 psig. For this distillation, the temperature may range from about −41° F. to about 154° F., preferably from about 59° F. to about 117° F., and more preferably from about 76° F. to about 80° F. For this distillation, the reflux ratio may range from about 0.3:1 to about 50:1, preferably from about 0.5:1 to about 10:1 and more preferably from about 0.7:1 to about 1:1. For this distillation the number of distillation stages may range from about 20 to about 200, preferably from about 30 to about 100 and more preferably from about 40 to about 60.

Recovered 1,1,1,2-tetrafluoroethane may be used as a propellant for a pharmaceutical agent in a pressurized metered dose inhaler whose construction is well known in the art. Suitable pharmaceutical agents non-exclusively include:

(1) steroid drugs such as, for example, beclomethasone, betamethasone, dexamethasone, fluticasone, hydrocortisone, budesonide, flunisolide, triamcinolone flumethasone, and prednisolone;

(2) antibiotic and antibacterial agents such as, for example, neomycin, mupirocin and chlorhexidine;

(3) systemically active drugs such as, for example, isosorbide dinitrate, isosorbide mononitrate, apomorphine and nicotine;

(4) antihistamines such as, for example, azelastine, chlorpheniramine, astemizole and terfenadine;

(5) anti-inflammatory agents such as, for example, piroxicam, nedocromil, cromoglycate, fasafungine and iodoxamide;

(6) anticholinergic agents such as, for example, ipratropium bromide and oxitroprium bromide;

(7) anti-emetics such as, for example, domperidone, hyoscine, cinnarizine metoclopramide, cyclizine, dimenhydrinate and promethazine;

(8) hormonal drugs such as, for example, vasopressin or desmopressin;

(9) bronchodilators, such as salbutamol, fenoterol and salmeterol;

(10) sympathomimetic drugs, such as tramazoline and xylometazoline;

(11) anti-fungal drugs such as miconazole;

(12) local anaesthetics such as benzocaine and lignocaine;

(13) opiates, preferably for pain management, such as buprenorphine, dextromoramide diamorphine, fentanyl, methadone, morphine, oxycodone, phenazocine, pethidine and combinations thereof with an anti-emetic;

(14) analgesics and drugs for treating migraine such as clonidine, codine, coproxamol, dextropropoxypene, ergotamine, sumatriptan, tramadol and non-steroidal antiflammatory drugs;
(15) narcotic agonists and opiate antidotes such as naloxone, and pentazocine;
(16) phosphodiesterase type 5 inhibitors, such as sildenafil (viagra); and
(17) pharmaceutically acceptable salts of any of the foregoing.

Recovered chlorodifluoromethane may be used to produce tetrafluoroethylene monomer. Such a technique is well known in the art. Likewise the polymerization of tetrafluoroethylene to polytetrafluoroethylene is well known in the art.

The following non-limiting examples serve to illustrate the invention.

EXAMPLE 1

100 grams of refrigerant grade HFC-134a containing approximately 20 ppmw of methyl chloride was charged into a laboratory sample cylinder that was pre-charged with molecular sieve 4A. The mixture was shaken and the resulting HFC-134a was analyzed. Methyl chloride was not detected in the HFC-134a sample.

EXAMPLE 2

A drying vessel was charged with approximately 700 pounds of molecular sieve 4A. Refrigerant grade HFC-134a containing 20 ppmw of methyl chloride was circulated through the vessel for several hours. The HFC-134a was then reanalyzed. Methyl chloride was not detected in the HFC-134a sample.

EXAMPLE 3

A drying vessel was charged with approximately 700 pounds of molecular sieve 4A. Refrigerant grade HFC-134a containing 20 ppmw of methyl chloride was pumped through the vessel in a one-pass operation to a shipping vessel. The HFC-134a in the shipping vessel was analyzed and methyl chloride was not detected.

EXAMPLES 4-6

Examples 1-3 are repeated except HCFC-22 is substituted for HFC-134a. Similar results are noted.

While the present invention has been particularly shown and described with reference to preferred embodiments, it will be readily appreciated by those of ordinary skill in the art that various changes and modifications may be made without departing from the spirit and scope of the invention. It is intended that the claims be interpreted to cover the disclosed embodiment, those alternatives which have been discussed above and all equivalents thereto.

What is claimed is:

1. A method for separating 1,1,1,2-tetrafluoroethane from a mixture comprising 1,1,1,2-tetrafluoroethane and methyl chloride which comprises contacting a mixture comprising 1,1,1,2-tetrafluoroethane and methyl chloride with a zeolite under conditions sufficient to remove the methyl chloride and then recovering from said contacted mixture substantially purified 1,1,1,2-tetrafluoroethane.

2. The method of claim 1 further comprising the subsequent step of distilling the substantially purified 1,1,1,2-tetrafluoroethane at least once.

3. The method of claim 1 further comprising the subsequent step of distilling the substantially purified 1,1,1,2-tetrafluoroethane under conditions sufficient to remove impurities having a higher boiling point than 1,1,1,2-tetrafluoroethane.

4. The method or claim 1 further comprising the subsequent step of distilling the substantially purified 1,1,1,2-tetrafluoroethane under conditions sufficient to remove impurities having a lower boiling point than 1,1,1,2-tetrafluoroethane.

5. The method of claim 1 further comprising the subsequent steps of distilling the substantially purified 1,1,1,2-tetrafluoroethane at least twice, and in either order, a first distillation step under conditions sufficient to remove impurities having a lower boiling point than 1,1,1,2-tetrafluoroethane; and a second distillation step under conditions sufficient to remove impurities having a higher boiling point than 1,1,1,2-tetrafluoroethane.

6. The method of claim 1 further comprising the subsequent step of distilling the substantially purified 1,1,1,2-tetrafluoroethane at least once and then contacting the substantially purified 1,1,1,2-tetrafluoroethane with a zeolite.

7. The method of claim 1 further comprising the subsequent step of distilling the substantially purified 1,1,1,2-tetrafluoroethane under conditions sufficient to remove impurities having a higher boiling point than 1,1,1,2-tetrafluoroethane and then contacting the substantially purified 1,1,1,2-tetrafluoroethane with a zeolite.

8. The method of claim 1 further comprising the subsequent stop of distilling the substantially purified 1,1,1,2-tetrafluoroethane under conditions sufficient to remove impurities having a lower boiling point than 1,1,1,2-tetrafluoroethane and then contacting the substantially purified 1,1,1,2-tetrafluoroethane with a zeolite.

9. The method of claim 1 further comprising the subsequent steps of distilling the substantially purified 1,1,1,2-tetrafluoroethane at least twice, and in either order, a first distillation step under conditions sufficient to remove impurities having a lower boiling point than 1,1,1,2-tetrafluoroethane; and a second distillation step under conditions sufficient to remove impurities having a higher boiling point than 1,1,1,2-tetrafluoroethane; and then contacting the substantially purified 1,1,1,2-tetrafluoroethane with a zeolite.

10. The method of claim 1 further comprising the previous step of distilling the mixture comprising 1,1,1,2-tetrafluoroethane and methyl chloride at least once.

11. The method of claim 1 further comprising the previous step of distilling the mixture comprising 1,1,1,2-tetrafluoroethane and methyl chloride under conditions sufficient to remove impurities having a higher boiling point than 1,1,1,2-tetrafluoroethane.

12. The method of claim 1 further comprising the previous step of distilling the mixture comprising 1,1,1,2-tetrafluoroethane and methyl chloride under conditions sufficient lower boiling point than 1,1,1,2-tetrafluoroethane.

13. The method of claim 1 further comprising the previous steps of distilling the mixture comprising 1,1,1,2-tetrafluoroethane and methyl chloride at least twice, and in either order, a first distillation step under conditions sufficient to remove impurities having a lower boiling point than 1,1,1,2-tetrafluoroethane; and a second distillation step under conditions sufficient to remove impurities having a higher boiling point than 1,1,1,2-tetrafluoroethane.

14. The method of claim 5 further comprising the previous steps of distilling the mixture comprising 1,1,1,2-tetrafluoroethane and methyl chloride at least twice, and in either order, a first distillation step under conditions sufficient to remove impurities having a lower boiling point than 1,1,1,2-tetrafluoroethane; and a second distillation step under conditions sufficient to remove impurities having a higher boiling point than 1,1,1,2-tetrafluoroethane.

15. The method or claim 1 wherein the substantially purified 1,1,1,2-tetrafluoroethane contains about 5 ppmw of methyl chloride or less.

16. The method of claim 1 wherein the substantially purified 1,1,1,2-tetrafluoroethane contains about 1 ppmw of methyl chloride or less.

17. The method of claim 1 wherein the substantially purified 1,1,1,2-tetrafluoroethane contains about 0 ppmw of methyl chloride.

18. The method of claim 1 wherein the zeolite is a molecular sieve.

19. The method of claim 1 wherein the zeolite comprises $Na_2O$—$Al_2O_3$-$2SiO_2$-$nH_2O$.

20. A method for preparing a pharmaceutical delivery form which comprises combining the substantially purified 1,1,1,2-tetrafluoroethane produced according to claim 1 with a therapeutically effective amount of a pharmaceutical composition.

21. A method for preparing a pharmaceutical delivery form which comprises combining the substantially purified 1,1,1,2-tetrafluoroethane produced according to claim 2 with a therapeutically effective amount of a pharmaceutical composition.

22. A method for preparing a pharmaceutical delivery form which comprises combining the substantially purified 1,1,1,2-tetrafluoroethane of produced according to claim 13 with a therapeutically effective amount of a pharmaceutical composition.

23. A method for separating chlorodifluoromethane from a mixture comprising chlorodifluoromethane and methyl chloride which comprises contacting a mixture comprising chlorodifluoromethane and methyl chloride with a zeolite under conditions sufficient to remove the methyl chloride and then recovering from said contacted mixture substantially purified chlorodifluoromethane.

24. The method of claim 23 further comprising the subsequent step of distilling the substantially purified chlorodifluoromethane at least once.

25. The method of claim 23 further comprising the subsequent step of distilling the substantially purified chlorodifluoromethane under conditions sufficient to remove impurities having a higher boiling point than chlorodifluoromethane.

26. The method of claim 23 further comprising the subsequent step of distilling the substantially purified chlorodifluoromethane under conditions sufficient to remove impurities having a lower boiling point than chlorodifluoromethane.

27. The method or claim 23 further comprising the subsequent steps of distilling the substantially purified chlorodifluoromethane at least twice, and in either order, a first distillation step under conditions sufficient to remove impurities having a lower boiling point than chlorodifluoromethane; and a second distillation step under conditions sufficient to remove impurities having a higher boiling point than chlorodifluoromethane.

28. The method claim 23 further comprising the subsequent step of distilling the substantially purified chlorodifluoromethane at least once and then contacting die substantially purified chlorodifluoromethane with a zeolite.

29. The method of claim 23 further comprising the subsequent step of distilling the substantially purified chlorodifluoromethane under conditions sufficient to remove impurities having a higher boiling point than chlorodifluoromethane and then contacting the substantially purified chlorodifluoromethane with a zeolite.

30. The method of claim 23 further comprising the subsequent step of distilling the substantially purified chlorodifluoromethane under conditions sufficient to remove impurities having a lower boiling point than chlorodifluoromethane and then contacting the substantially purified chlorodifluoromethane with a zeolite.

31. The method of claim 23 further comprising the subsequent steps of distilling the substantially purified chlorodifluoromethane at least twice, and in either order, a first distillation step under conditions sufficient to remove impurities having a lower boiling point than chlorodifluoromethane; and a second distillation step under conditions sufficient to remove impurities having a higher boiling point than chlorodifluoromethane; and then contacting the substantially purified chlorodifluoromethane with a zeolite.

32. The method of claim 23 further comprising the previous step of distilling the mixture comprising chlorodifluoromethane and methyl chloride at least once.

33. The method of claim 23 further comprising the previous step of distilling the mixture comprising chlorodifluoromethane and methyl chloride under conditions sufficient to remove impurities having a higher boiling point than chlorodifluoromethane.

34. The method of claim 23 further comprising the previous step of distilling the mixture comprising chlorodifluoromethane and methyl chloride under conditions sufficient to remove impurities having a lower boiling point than chlorodifluoromethane.

35. The method of claim 23 further comprising the previous steps of distilling the mixture comprising chlorodifluoromethane and methyl chloride at least twice, and in either order, a first distillation step under conditions sufficient to remove impurities having a lower boiling point than chlorodifluoromethane; and a second distillation step under conditions sufficient to remove impurities having a higher boiling point than chlorodifluoromethane.

36. The method of claim 27 further comprising the previous steps of distilling the mixture comprising chlorodifluoromethane and methyl chloride at least twice, and in either order, a first distillation step under conditions sufficient to remove impurities having a lower boiling point than chlorodifluoromethane; and a second distillation step under conditions sufficient to remove impurities having a higher boiling point than chlorodifluoromethane.

37. The method of claim 23 the substantially purified chlorodifluoromethane contains about 5 ppmw of methyl chloride or less.

38. The method of claim 23 wherein the substantially purified chlorodifluoromethane contains about 1 ppmw of methyl chloride or less.

39. The method of claim 23 wherein the substantially purified chlorodifluoromethane contains about 0 ppmw of methyl chloride.

40. The method of claim 23 wherein the zeolite is a molecular sieve.

41. The method or claim 23 wherein the zeolite comprises $Na_2O$—$Al_2O_3$-$2SiO_2$-$nH_2O$.

* * * * *